(12) United States Patent
Neudl et al.

(10) Patent No.: US 10,905,813 B2
(45) Date of Patent: *Feb. 2, 2021

(54) MEMBRANE CATHETER

(71) Applicant: CCORE TECHNOLOGY GMBH, Vienna (AT)

(72) Inventors: Susanna Neudl, Vienna (AT); Roman Ullrich, Vienna (AT); Claus-Georg Krenn, Mödling (AT); Christoph Janeczek, Felixdorf (AT); Margit Gföhler, Vienna (AT)

(73) Assignee: CCORE TECHNOLOGY GMBH, Vienna (AT)

( * ) Notice: Subject to any disclaimer, the term of this patent is extended or adjusted under 35 U.S.C. 154(b) by 228 days.

This patent is subject to a terminal disclaimer.

(21) Appl. No.: 15/768,705

(22) PCT Filed: Oct. 14, 2016

(86) PCT No.: PCT/EP2016/074776
§ 371 (c)(1),
(2) Date: Apr. 16, 2018

(87) PCT Pub. No.: WO2017/064285
PCT Pub. Date: Apr. 20, 2017

(65) Prior Publication Data
US 2018/0214055 A1 Aug. 2, 2018

(30) Foreign Application Priority Data
Oct. 14, 2015 (EP) .................................... 15189777

(51) Int. Cl.
*A61M 1/10* (2006.01)
*A61M 1/16* (2006.01)
(Continued)

(52) U.S. Cl.
CPC ....... *A61M 1/1678* (2013.01); *A61B 5/14525* (2013.01); *A61M 1/1032* (2014.02);
(Continued)

(58) Field of Classification Search
CPC ............ A61B 5/14525; A61B 5/14528; A61B 5/14532; A61B 5/6852; A61M 1/1029;
(Continued)

(56) References Cited

U.S. PATENT DOCUMENTS 4,631,053 A 12/1986 Taheri
9,446,179 B2 * 9/2016 Keenan .................... A61M 1/10
(Continued)

FOREIGN PATENT DOCUMENTS

GB 2004092 3/1979
GB 2505068 2/2014
(Continued)

OTHER PUBLICATIONS

International Search Report dated Dec. 23, 2016 issued in PCT International Patent Application No. PCT/EP2016/074776, 10 pp.
(Continued)

*Primary Examiner* — Philip R Wiest
(74) *Attorney, Agent, or Firm* — Nixon & Vanderhye P.C.

(57) ABSTRACT

A catheter for intravascular use has a blood inlet and a blood outlet, and includes a membrane arranged in the catheter in such a way that at least one part of the blood flowing into the catheter via the blood inlet during operation comes into contact with the membrane. The membrane allows an exchange of at least one substance between a carrier medium and the blood. The carrier medium is a carrier fluid in which the substance to be exchanged can be dissolved, and the catheter includes a delivery device that is designed to at least partially compensate for a pressure difference between the blood inlet and the blood outlet during operation. A method
(Continued)

Figure 6:
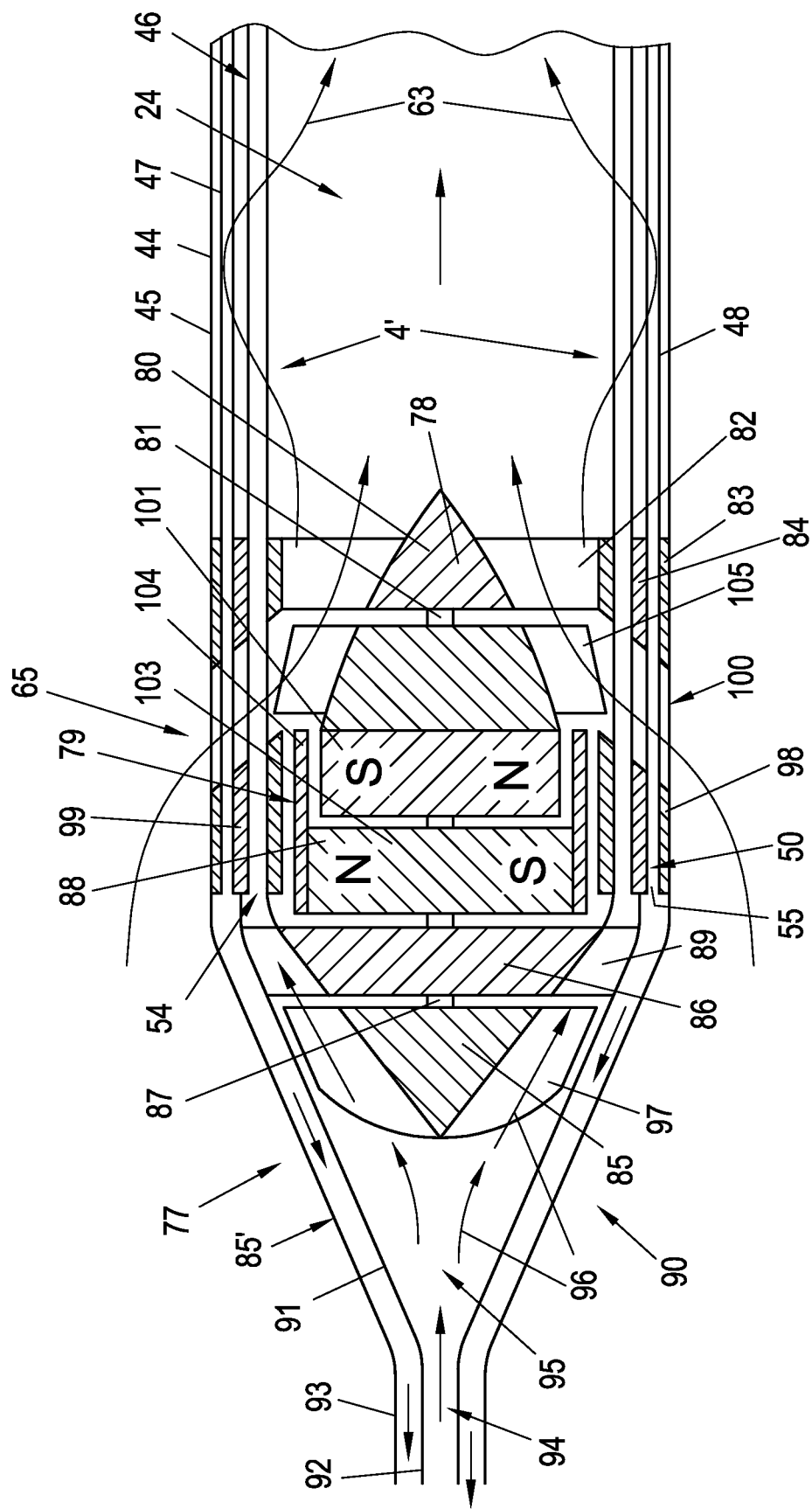

for removing at least one substance from venous blood for diagnostic purposes uses a device of this type.

13 Claims, 4 Drawing Sheets

(51) Int. Cl.
*A61B 5/145* (2006.01)
*A61B 5/00* (2006.01)
*A61M 1/36* (2006.01)
*B01D 63/08* (2006.01)

(52) U.S. Cl.
CPC ....... *A61M 1/1036* (2014.02); *A61B 5/14532* (2013.01); *A61B 5/6852* (2013.01); *A61M 1/3679* (2013.01); *B01D 63/087* (2013.01)

(58) Field of Classification Search
CPC .............. A61M 1/1031; A61M 1/1032; A61M 1/1036; A61M 1/1678
See application file for complete search history.

(56) References Cited

U.S. PATENT DOCUMENTS

| | | | |
|---|---|---|---|
| 2008/0014622 A1 | 1/2008 | Federspiel et al. | |
| 2009/0254022 A1* | 10/2009 | Cattaneo | A61M 1/1678 604/26 |
| 2010/0258116 A1* | 10/2010 | Federspiel | A61M 1/1698 128/200.25 |
| 2011/0011786 A1 | 1/2011 | Feichtner et al. | |
| 2013/0053623 A1* | 2/2013 | Evans | A61M 1/101 600/16 |
| 2014/0010686 A1 | 1/2014 | Tanner et al. | |
| 2014/0275726 A1* | 9/2014 | Zeng | A61M 1/1012 600/16 |
| 2016/0000983 A1* | 1/2016 | Mohl | A61M 1/1086 600/17 |
| 2017/0080136 A1* | 3/2017 | Janeczek | A61M 1/12 |
| 2018/0228950 A1* | 8/2018 | Janeczek | A61M 1/1006 |

FOREIGN PATENT DOCUMENTS

| | | |
|---|---|---|
| JP | 4-180771 A | 6/1992 |
| JP | 2005-538758 A | 12/2005 |
| JP | 2011-517102 A | 5/2011 |
| JP | 2015-500666 A | 1/2015 |
| WO | WO 2004/016300 | 2/2004 |
| WO | WO 2008/046630 | 4/2008 |

OTHER PUBLICATIONS

European Search Report dated Mar. 22, 2016 issued in European Patent Application No. 15189777.4, 10 pp.

Moinard-Chécot, Delphine et al., "Mechanism of Nanocapsules Formation by the Emulsion-Diffusion Process," Journal of Colloid and Interface Science 317 (2008), pp. 458-468.

Vericella, John J. et al., "Encapsulated Liquid Sorbets for Carbon Dioxide Capture," Nature Communications, 6:6124, DOI: 10.1038/ncomms7124, Feb. 5, 2015, pp. 1-7.

Erdmann, Christian et al., "Permeability Profile of Poly(Alkyl Cyanoacrylate) Nanocapsules," Journal of Colloid and Interface Science 478 (2016), pp. 394-401.

Utada, A.S. et al, "Monodisperse Double Emulsions Generated from a Microcapillary Device," Science, vol. 308, Apr. 22, 2005, pp. 537-541.

Japanese Office Action dated Oct. 13, 2020 issued in Japanese Patent Application No. 2018-519428 and English translation, 6 pp.

\* cited by examiner

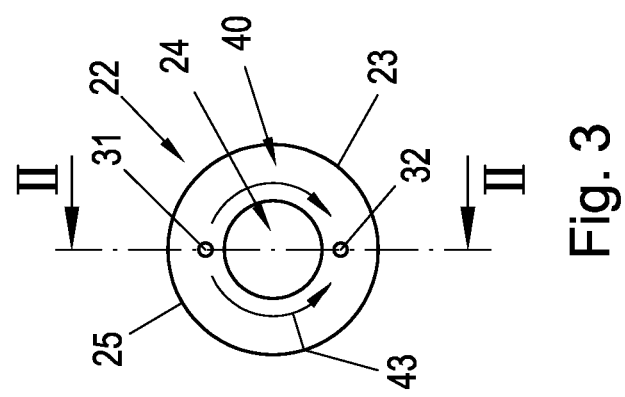
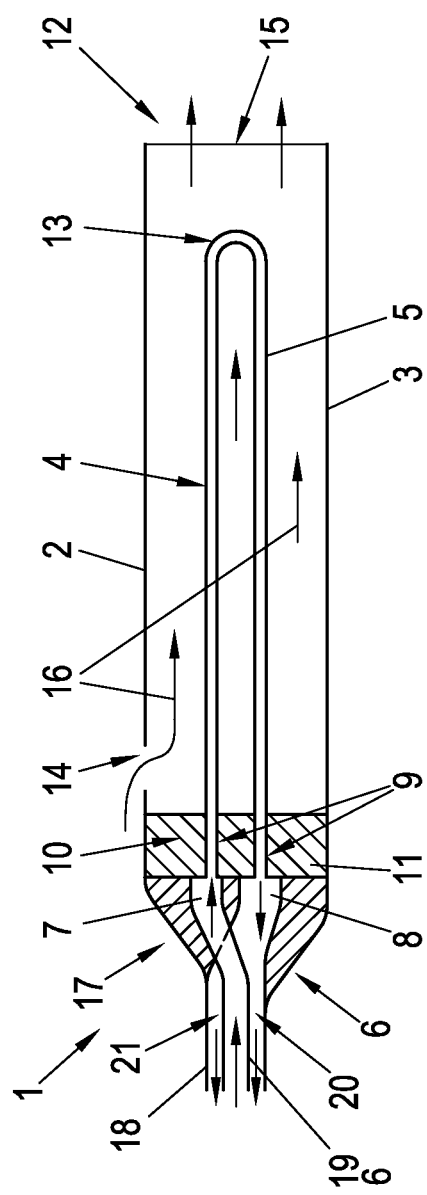
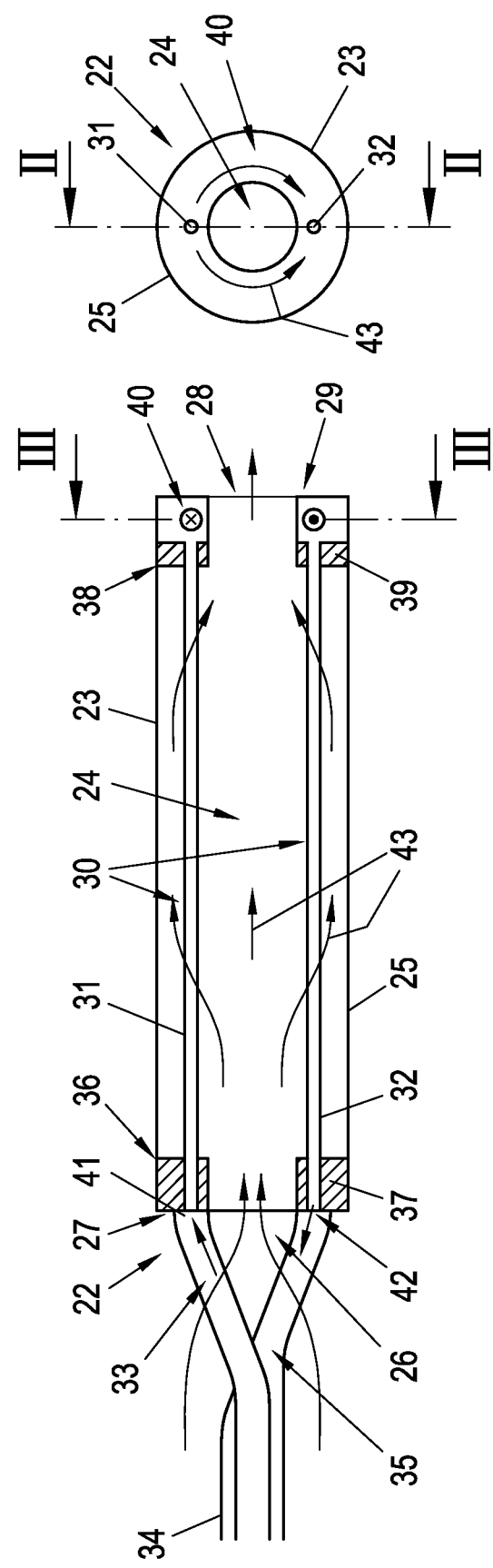

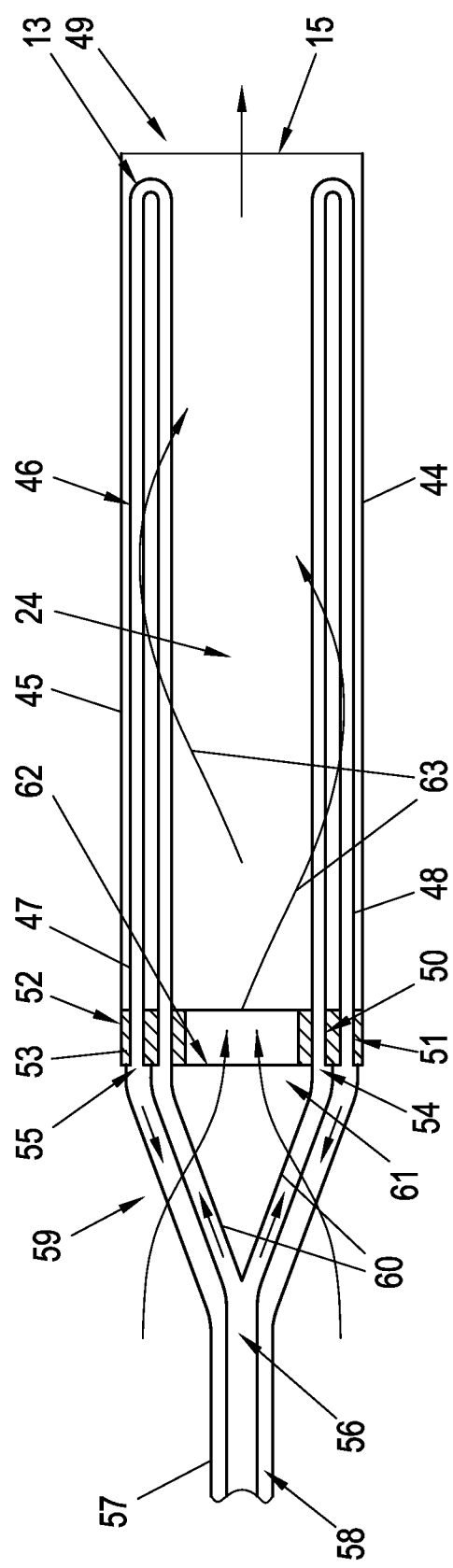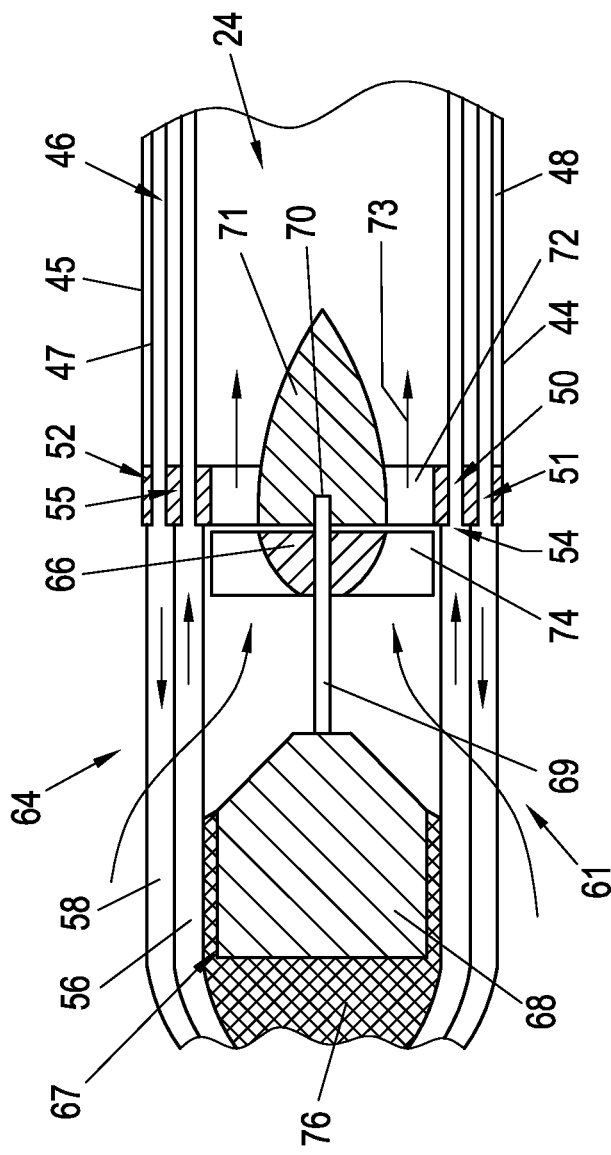

MEMBRANE CATHETER

This application is the U.S. national phase of International Application No. PCT/EP2016/074776 filed Oct. 14, 2016 which designated the U.S. and claims priority to European Patent Application No. 15189777.4 filed Oct. 14, 2015, the entire contents of each of which are hereby incorporated by reference.

The invention relates to a device for the exchange or replacement of substances from the blood or into the blood.

The field of application of the invention in general is the examination or treatment of the human or animal body. In detail, in this connection the transport of certain substances either from the blood of the body to the outside of the body or—vice versa—from the outside of the body into the blood of the body is enabled. In particular diagnostic methods which are based on evidence of certain substances in the blood or also on the quantitative measuring of certain substances in the blood fall within said general field of application. Furthermore, the field of application of the invention also includes functions which support or replace the activity of organs in the body, in particular of the lung, the kidneys or the liver. Eventually, the invention can also be used for the administration of non-endogenous substances, in particular drugs or medicaments. Especially promising fields of application concern a long-time support of the pulmonary function or of the renal function (Continuous Renal Replacement Therapy, CRRT).

To the above field of application there also belongs for instance an extracorporeal blood purification (ECBP) which refers to the removal of endogenous or exogenous toxins or of dissolved substances from the blood and also comprises various therapies like hemodialysis, hemofiltration, or hemodiafiltration. The main idea is the withdrawal of blood from the patient, the removal of the substance in an external filtering unit ("purification") and the return of purified blood via a venous access.

GB 2 004 092 A shows a device for measuring the content of glucose in the blood by means of an intravascular membrane catheter. In this connection, in a circuit a measuring liquid is guided past a membrane forming the outer side of the catheter and is transferred out of the body, where first of all oxygen is added to the liquid. Then the measuring liquid is supplied to an enzyme reactor, and the concentration of glucose in the blood is determined from the partial pressure of oxygen at the outlet of the reactor. Here, in this design, the surface of the membrane is limited by the dimensions of the catheter so that only a comparably low amount of the blood comes into contact with the membrane and participates in the exchange with the measuring liquid.

WO 2008/046630 A1 shows devices for the continuous monitoring of the concentration of a substance in the blood by means of microdialysis. Here a tubular membrane which is surrounded by blood and through which a perfusate flows can be used. Such a tubular membrane, naturally, has no blood inlet or blood outlet. As an alternative to the tubular membrane, a planar membrane is described, wherein blood and a carrier medium are pumped—obviously in an extracorporeal manner—through lines provided respectively on opposing sides of the planar membrane and extending in meanders.

Furthermore, in the field of the invention it has already been known to support the pulmonary function of a patient by means of ECMO (Extra Corporeal Membrane Oxygenation) systems or ECCO2R (Extra Corporeal $CO_2$ Removal) systems. Such systems usually comprise cannulas, an impeller pump, a tube system, a membrane oxygenator, safety systems, and a heat exchanger, and they are reliable and easy to handle. They do, however, have several limitations with regard to a wide distribution and frequent use—they are very expensive, quite large in size and make patients immobile, which means that the patient has to be immobilized (sedated) during the treatment as there is the risk that the cannulas can become dislocated due to movements of the patient. Furthermore, in the common systems a conducting of the blood out of the body via one or several catheters and a return of the blood—to which oxygen has been added and from which $CO_2$ has been removed—into the body are required.

Therefore, a lot of patients with an acute and chronic respiratory increase of $CO_2$ (hypercapnia) would benefit from the availability of a mobile form of the ECCO2R reduced in size—with all advantages to be expected—as thereby they can be mobilized at an earlier point of time, they to not need long-lasting or further sedations, and said therapy could also be used already at an early phase of the disease. In extenso, a complete avoidance of a mechanical ventilation is conceivable, as a major part of the patients requires ventilation only due to the respiratory exhaustion and the hypercapnia as a result of the increased breathing work.

Already marketable intravascular membrane oxygenators had undergone clinical trials in the past and were approved for use with patients. Said techniques primarily had the object to improve the shortage of oxygen in the blood by an intravascular membrane oxygenation or to guarantee a sufficient availability of oxygen. In order to achieve said object, a large contact surface between the blood and the gas phase as well as a supply of gases into the catheter in the vascular system is required which potentially increases the risk of a gas embolism severely. The problem of the required large minimum surface was solved by the introduction of unfoldable webs of hollow fibres which were flushed extracorporeally with high gas flows. Said technique has several limitations, among them a low gas transfer for oxygen ($O_2$), a high thrombogenicity of the fibre system having a turbulent flow therethrough, the susceptibility of the hollow fibres to breaking, and the obligatory size of the catheter with all of the associated risks of injuries. For this reason, said technology could not achieve acceptance in hospitals.

Intravascular membrane oxygenators are known in different design variants from patent literature. For instance WO 2004/016300 A2 discloses an intravenous oxygenator in the form of a catheter for oxygenating the blood, said oxygenator comprising a fibre bundle, said fibres being respectively connected by a first connection to a gas supply and by a second connection to a gas outlet. The fibre bundle is twisted about the longitudinal axis of the oxygenator during operation by a relative rotation of the first connection of the fibres in relation to the second connection of the fibres. Consequently, the fibres extend over the entire length of the fibre bundle as continuous gas conduits. During operation of the oxygenator, oxygen is supplied which flows via the first connection into the fibres at the surfaces of which a diffuse gas exchange with the blood takes place. Thereby an enrichment of the blood with oxygen and a simultaneous removal of $CO_2$ is obtained. Therefore, at the second connection there is present a gas mixture of oxygen and carbon dioxide in the fibres, said gas mixture flowing through a discharge chamber in a tube and through the tube out of the body of the patient. The blood flowing into the oxygenator flows through the twisted fibre bundle and gets to a pump where the blood is transported in the flow direction of the vein and leaves the oxygenator through an outlet. Therefore, the drop in pressure of the blood is compensated for by the pump so that the pressure at the outlet once again has the physiological pressure. An effective exchange of oxygen for carbon dioxide requires a very large membrane surface of the hollow fibres which is hardly realizable in a catheter, and which, in turn, further increases the risk of the event of a gas embolism.

US 2010/0258116 A1 deals with different methods for the removal of carbon dioxide and in particular with blood oxygenators. Therein, however, there cannot be found any detailed explanations with regard to certain exchange devices, and there are mentioned extracorporeal exchange devices as well as intravascular catheters. The structure of the catheter is not described in detail. There is in particular not shown any catheter with a blood inlet and a blood outlet. Furthermore, with regard to catheters only the supply of gas as an exchange medium is mentioned.

U.S. Pat. No. 4,631,053 A discloses an intravascular membrane oxygenator. As an exchange medium there is exclusively disclosed the use of oxygen which is gaseous under standard conditions. A carrier medium is apparently not used, as only a supply line for the oxygen and no return for a possible carrier medium is shown.

In GB 2 505 068 A there is shown an extracorporeal drive which is connected via a shaft with a catheter pump for supporting the heart function. Obviously, due to its size the disclosed drive unit is unsuited for being used as a part of an intravascular catheter.

The pump shown in US 2013/053623 A1 is used for the support of the heart function and, thus, refers to a completely different field of application than the present device. The shown pump, naturally, does not comprise a membrane in the sense of the device according to the invention, i.e. for the exchange of substances.

Based on the mentioned disadvantages of the known devices and methods it is an object of the invention to provide a device or a method by means of which substances can be transported efficiently out of the blood or into the blood. Furthermore, said device shall meet the criteria of minimally invasive surgeries and shall affect the patient and his/her blood circulation as little as possible. In particular, the disadvantages of an extracorporeal circuit or circulation and unnecessary surface contacts of the blood shall be reduced. Furthermore, the removal of toxic substances from the blood shall be improved in contrast to methods currently in use. For instance, by the system according to the invention the risk of a gas embolism shall be reduced and at the same time the performance of the exchange device, in particular with regard to the ratio between the rate of exchange of the membrane and the size of the catheter required to achieve this, shall be improved.

Consequently, the present invention refers to a device comprising a catheter for intravascular use, wherein the catheter has a blood inlet and a blood outlet, and comprises a membrane, wherein a first side of the membrane is in contact with a carrier medium and wherein the membrane is arranged in the catheter in such a way that at least one part of the blood flowing into the catheter via the blood inlet during operation comes into contact with a second side of the membrane lying opposite the first side thereof, before the blood leaves the catheter via the blood outlet, wherein the membrane allows an exchange of at least one substance to be exchanged between the carrier medium and the blood. In particular, in the respective device the catheter can comprise a conveying device which is configured to at least partially compensate for a pressure difference between the blood inlet and the blood outlet.

The invention also refers to a device comprising a catheter for intravascular use, wherein the catheter has a blood inlet and a blood outlet, and comprises a membrane, wherein a first side of the membrane delimits a lumen for the reception of a carrier medium, and wherein the membrane is arranged in the catheter in such a way that at least one part of the blood flowing into the catheter via the blood inlet during operation comes into contact with a second side of the membrane lying opposite the first side thereof, before the blood leaves the catheter via the blood outlet, wherein the membrane allows an exchange of at least one substance to be exchanged between a carrier medium received in the lumen during operation and the blood, and wherein the catheter comprises a conveying device which is configured to at least partially compensate for a pressure difference between the blood inlet and the blood outlet during operation.

Furthermore, the invention refers to a method for removing at least one substance from venous blood for diagnostic purposes using one of the above-mentioned devices, wherein the substance to be removed corresponds to the substance to be exchanged through the membrane of the catheter of the device.

Furthermore, the invention refers to a method for the treatment of a human or animal body by replacing or exchanging at least one substance from the blood or into the blood using one of the above-mentioned devices.

Correspondingly, according to the invention it is provided that the carrier medium is a carrier liquid in which the substance to be exchanged can be dissolved. That means that the carrier medium is in a liquid state of matter during operation (in case of standard conditions). Due to the use of a liquid as a carrier medium, the removal and supply of substances can be performed in a substantially more controlled and more efficient manner; thereby for instance the risk of a gas embolism is reduced significantly. Furthermore, there is only a slight risk of the development of thromboses. As the blood is not conducted out of the patient, the necessity of a systemic anticoagulation with the bleeding complications associated therewith is eliminated. Apart therefrom, by the use of suitable carrier liquids and a faster/higher circulation, a in general higher exchange of the substance to be exchanged through the membrane, i.e. through a membrane which is suitable for liquids (in short: "liquids membrane"), can be achieved, and, thus, the required membrane surface can be reduced which results in a reduced pressure difference in the catheter. If the catheter comprises a conveying device, the conveying rate of the conveying device required for the adaptation of the lower pressure difference is also reduced accordingly, which, in general, allows for a reduction in size of the conveying device and, hence, of the catheter as a whole. In case of a catheter without any conveying device, a reduction of the cross-section of the catheter can be carried out due to the comparatively lower pressure difference. By the possibility of the reduction in size of the entire system, which is associated with the present invention, the application is facilitated, and thereby, in the end, the risk of complications is reduced. By using components already available on the market, the entire system can be dimensioned such that it is portable and that the extracorporeal circuit with or at the console even fits into a bag.

Owing to the use of a carrier liquid as a carrier medium, the membrane of the device is a membrane which is suitable for liquids, i.e. which is configured and designed for the exchange of substances between two liquids. Even if with such a membrane also an exchange of substances between a liquid and a gas could be achieved or can be achieved to a certain degree, from the configuration of the membrane as a whole and above all from the provided contact surface and/or from the mechanical stability it results that the membrane is not designed for the use with a gaseous carrier medium.

In a particularly small and, hence, advantageous type of construction, the conveying device comprises a drive unit for the generation of a torque and a pump rotor or impeller connected to the drive unit for transmitting a torque. In this connection, the torque is preferably transmitted along a shaft the axis of which is arranged substantially in parallel to a longitudinal axis of extension of the catheter. Here, the pump rotor corresponds to the impeller of an axial-flow pump.

A simple control of the conveying device, in particular of the rotational speed of the rotor, can be achieved if the conveying device comprises an electric motor. In this connection, the reliability of the conveying device is substantially limited by the reliability of the electric motor.

Alternatively, the conveying device can comprise a turbine element around which the carrier medium flows during operation. In such a conveying device, a part of the flow energy of the carrier medium is transferred onto the delivered blood. In the simplest and most reliable case, the turbine element is directly coupled to the pump rotor so that the two elements will run with the same rotational speed during operation. In this connection, a driving relationship can be determined by means of the shape, i.e. the surface, the form and the arrangement, of the respective blades. Said type of drive has the additional advantage that no separate power supply, in particular no electrical connection, of the drive unit from outside of the body is required. Thereby the reliability as well as also the operating safety of the device are improved.

In connection with the drive unit it is favourable if the pump rotor is connected to the drive unit via a magnetic coupling, wherein the magnetic coupling comprises two coupling parts for the transmission of the torque along an axis of rotation being rotatable relative to each other and each including a permanent magnet. As a magnetic coupling there can for instance be used a concentric ring coupling or a disc coupling. When compared to a continuous mechanical connection, for instance in the form of a continuous shaft, a magnetic coupling has the advantage that the transmitted torque is limited. Thereby, in particular in case of an error, unplanned states can be excluded; for instance, even in case of a blockade of one element, the respectively coupled other element can still remain movable—with certain restrictions. If for instance the drive of the pump rotor fails or blocks, after overcoming the torque maximally transmitted by the magnetic coupling the pump rotor can run almost freely, whereby, in comparison with a blocking pump rotor, the blood flow is subjected to a smaller flow resistance so that the risk of complications as for instance of thromboses due to the blood coagulation (activated at external or foreign surfaces) is reduced. Moreover, by the limitation of the torque it is also possible to counteract a damaging of the pump.

Furthermore, the impeller or rotor of the pump thus formed can also be supported preferably in a suspended manner. There can for instance be provided a bearing in accordance with the heart support system INCOR of the "Berlin Heart" company.

In order to be able to transmit a desired torque also in a particularly compact magnetic coupling, it has proven favourable if one of the coupling parts comprises an at least partially ferromagnetic guiding element which is non-rotatably connected to the permanent magnet of the coupling part, wherein one part of the guiding element is disposed radially outside of the permanent magnet of the other coupling part. This means that the magnetic coupling comprises two coupling parts which can be rotated relative to each other, wherein a drive-side coupling part comprises a drive-side permanent magnet and wherein an output-side coupling part comprises an output-side permanent magnet that lies opposite and at a distance from the drive-side permanent magnet along the axis of rotation, wherein one of the coupling parts comprises an at least partially ferromagnetic guiding element which is non-rotatably connected to the permanent magnet of the coupling part, wherein one part of the guiding element is disposed radially outside of the opposite permanent magnet. When compared to conventional concentric ring couplings, said design has the advantage that the manufacturing thereof is easier and more economical, and that, on the whole, less coupling surface is required, as a part of the torque is transmitted via the front face of the coupling parts. When compared to conventional disc couplings, said design has the advantage that only smaller radial dimensions are required for the transmission of a certain torque. The guiding element may be shaped as a cup or a hollow cylinder—comparable to the outer coupling part of a concentric ring coupling—and may surround the respective other coupling part circumferentially, i.e. it preferably extends radially outside of both permanent magnets. In this connection, the guiding element may be formed as a thin-walled hollow cylinder, for example, so that with unchanged dimensions the magnetised volume of the disc coupling is retained to the greatest possible extent and, at the same time, a transmittable torque in a size comparable to that of a concentric ring coupling may be obtained between the guiding element and the opposite permanent magnet at a distance therefrom. The direction of magnetisation of the permanent magnets is preferably oriented perpendicularly to the axis of rotation, i.e. the poles of the magnets extend circumferentially from south to north and are—at least in a two-pole design—diametrically opposite each other with respect to the axis of rotation. By means of the guiding element, magnetic field lines extending radially from the permanent magnets are bundled, and due to the ferromagnetic material of the guiding element the magnetic force between the coupling parts is further increased. The magnetic force for transmitting the torque is raised by compressing the magnetic field lines in the ferromagnetic material. Advantageously, due to the larger volume of the permanent magnets when compared to concentric ring couplings with equal dimensions of the couplings, a shorter axial extension and, thus, lower radial transverse forces on the bearings of the coupling parts can be achieved.

The permanent magnets of the magnetic coupling can be 2-, 4-, or 6-pole permanent magnets, respectively. They are preferably each of a two-pole design with two half-cylindrical magnetic poles, respectively. The guiding element may comprise at least one diamagnetic separation parting the guiding element into at least two ferromagnetic sections in order to avoid a magnetic short circuit. In addition to the radial outer arrangement, the guiding element can also extend at a rear side of the non-rotatably connected permanent magnet, which rear side is facing away from the opposite permanent magnet. Alternatively or additionally, the guiding element can comprise a substantially H-shaped longitudinal section, with a cross web disposed perpendicularly to the axis of rotation and with cup-shaped recesses formed on both sides, wherein a permanent magnet is received and non-rotatably connected in one of these recesses. This means that the guiding element can comprise a hollow cylindrical jacket and can preferably be designed with an intermediate base arranged substantially at half height of the jacket.

A particularly high concentration of magnetic field lines within the guiding element of the magnetic coupling may be achieved if a diamagnetic shielding element is arranged at a rear side of the permanent magnet non-rotatably connected to the guiding element which rear side is facing away from the opposite permanent magnet. In this way, field lines running outside of the coupling parts may be avoided, and thus losses related thereto may be reduced.

Furthermore, it has proven favourable if, in the magnetic coupling, a diamagnetic shielding element is arranged at a front side of the permanent magnet non-rotatably connected to the guiding element which front side is facing the opposite permanent magnet, in particular in a region centred around the axis of rotation, which shielding element adjoins the guiding element preferably circumferentially or radially on the outside. Such a shielding makes it possible to guide and divert the magnetic field to regions located at larger radial distances from the axis of rotation so that the torque transmitted at a given magnetic force is increased.

In order to reliably avoid a transition of the carrier medium to the blood, it is also favourable for the two coupling parts to be hermetically separated. Such a hermetic separation may be obtained, for instance, by a hermetic wall between the two coupling parts of the magnetic coupling, which wall should be non-conductive both magnetically and electrically. In particular, at least one of the coupling parts can be accommodated in a substantially non-magnetic and electrically non-conductive housing so that it is possible to avoid losses due to a reversal of magnetism of the housing and/or induced eddy currents in the housing.

An application which profits in a particularly high extent from the advantages of the invention is the use for the removal of $CO_2$ from the blood, i.e. wherein the substance to be exchanged is $CO_2$. In this connection, the carrier liquid may have a solubility of at least 140 ml $CO_2$, in particular of at least 180 ml $CO_2$, in 100 ml of the carrier liquid at 37° C. In comparison therewith, the solubility of $CO_2$ in arterial blood at 40 mmHg (approximately 5332.88 Pa) (dissolved physically) is approximately 2.6 ml/100 ml and at 90 mmHg (11998.98 Pa) it is approximately 0.3 ml/100 ml.

The carrier liquid can be a perfluorocarbon or an albumin solution and/or an electrolyte solution, in particular enriched with specific proteins or glucose derivatives, or it can be a commercially available dialysate which preferably was additionally processed via an ion exchanger, activated carbon or another adsorber.

Preferably, the invention can be used with a dialysis liquid as a carrier medium, which comprises or consists of demineralized water including various electrolytes as well as bicarbonate in an identical concentration as the physiological extracellular liquid. During operation, the blood and the dialysis liquid can be guided in a counterflow along a semipermeable membrane which is permeable to low-molecular substances (<5-15 kDa or kilodaltons; related to the atomic mass unit Dalton) (uraemic toxins, electrolytes). Thereby a maximum concentration gradient can be obtained only for the excess uraemic toxins but not for the electrolytes. If additionally a liquid shall be separated, a pressure gradient can be generated which presses a solution off the blood. Thus, the invention can for instance be used in case of heavy metal poisonings and alcohol poisoning.

In connection with the exchange of $CO_2$ or the removal of $CO_2$ from the blood, a perfluorocarbon has turned out to be a particularly favourable carrier liquid. This means that the carrier liquid preferably is a liquid of the family of perfluorocarbons (PFC) which is in a liquid state under physiological conditions and at ambient temperature. PFC has a reception capacity for $CO_2$ which is ten times higher than that of blood (the solubility of $CO_2$ in PFC is 210 ml/dl, that of $O_2$ is 53 ml/dl). Apart from perfluorocarbons, in particular other blood substitutes, like for instance a haemoglobin based oxygen carrier, are suitable. The suitable perfluorocarbons further have a low surface tension and easily spread on surfaces due to their high spreading coefficient. Said properties and their large potential for the transport of $CO_2$ make said liquids particularly suitable for the use for flowing through a membrane of hollow fibres in order to remove above all a part of the continuously formed carbon dioxide for the relief of the breathing work during a spontaneous or mechanically supported ventilation under low blood flows. Therefore, the hollow fibre membrane will be preferably designed in such a way that the minimum exchange surface for an efficient $CO_2$ transfer is available which, for patients of normal weight and under blood flow rates of approximately 300 ml per minute (through the catheter/in conventional methods through the catheter—in the invention actually only contact equivalence time), lies in the order of magnitude of at least 0.84 m$^2$.

For the exchange of protein-bound toxins, the carrier liquid may preferably comprise albumin. In this case, the invention can be used for carrying out an albumin dialysis. In this connection, a membrane is used which is only permeable to toxins bound to the albumin and also is permeable to water-soluble small molecules. The concentration gradient of toxins on the blood circulation side is larger than on the side with the albumin-containing carrier liquid. Due to the concentration gradient and the permeability of the membrane to the albumin-bound toxins, said toxins pass through the membrane (diffusion) and are bound by the free albumin in the carrier liquid. Via a circuit, the albumin together with the toxins can travel on the dialysis side to different detoxification stations. As a first detoxification station there can for instance be provided a complete dialysis apparatus which, however, rather filters out the molecules dissolved in water (toxins) and checks the electrolyte level. As a second detoxification station there can be provided an activated carbon filter which filters toxins which are not anionic. Anionic toxins can leave the circuit via an anion filter. The albumin thus purified can then once again absorb toxins at the membrane. Thus, the albumin will become free again on the blood circulation side and can transport new toxins. The blood will be detoxified. As an alternative to the described reprocessing, the carrier liquid with the albumin can also be discarded after passing the membrane.

Furthermore, special carrier liquids (e.g. dialysates, physiological saline) can be prepared or mixed which are used for instance for the treatment of electrolyte disorders (hyperkaliemia) or for the transport of blood glucose, pathological glucose molecules (for the treatment of glycogen storage diseases), lipids (for the treatment of dyslipidoses), urea or creatinine, or in general for a therapeutic apheresis. In this connection, membranes, for instance semipermeable membranes, which are configured specifically for the exchange of the respective substance(s) can be used. Particularly preferred carrier liquids are, apart from perfluorocarbon, in particular albumin solutions and/or electrolyte solutions or commercially available dialysates which were additionally processed via an ion exchanger, activated carbon or another adsorber.

The invention can for instance be used as an artificial pancreas, wherein the blood can absorb insulin from the carrier liquid through the membrane and can pass on glucagon to the carrier liquid. The membrane can for instance be made of polyurethane.

When the above-mentioned carrier liquids are used, the invention enables that hypercapnia can be avoided in that a part of the continuously generated carbon dioxide is removed through a liquid, in particular a perfluorocarbon, for the relief of the breathing work during a spontaneous or mechanical ventilation. Perfluorocarbons show a high solubility not only for $CO_2$ but also for all respiratory gases and, therefore, also for $O_2$, $N_2$, and NO. Consequently, the surface for the exchange of gasses of the membrane used does not have to be as large as it is required for conventional intravascular membrane oxygenators. Thereby the catheter can be implemented in the size of a conventional dialysis catheter or a single port ECMO catheter. By the use of liquid perfluorocarbon, which has a gas binding capacity which is by far higher than that of oxygen used so far in conventional intravascular membrane oxygenators, for the achievement of a gas binding effect of similar quality a much smaller contact surface of the membrane with the blood is required in order to guarantee an efficient removal of $CO_2$.

Moreover, the invention can be used with a carrier liquid which includes decoupler substances. In general, toxins can be displaced by substances which have a higher affinity for the specific binding sites at the protein or at the lipid than the toxin. Said substances are called decoupler substances. As decoupler substances there are principally preferred physiological substances but, if necessary, also non-physiological substances which are regarded as toxicologically safe can be used. Said substances have a higher specific binding affinity to the binding sites of the toxin so that a shift of the chemical equilibrium is effected, and the toxins are released. Then the released toxins can be removed from the blood or from the blood components (enzymatically, adsorptively, membrane process).

For the removal of the released toxins from the carrier liquid there can be preferably used an ultrafiltration process. In this connection, solutions consisting of several components can be separated according to the molecular weight. Said process is suitable in particular for the separation of low-molecular substances. The exclusion limit, i.e. the molecular weight of the substances which are retained up to approximately 90%, is determined by the chosen membrane. The driving force is here a pressure difference between the two membrane sides. The obtained ultrafiltrate primarily contains the low-molecular substances, i.e. in general the toxin. There can, however, also be present small amounts of protein (approximately 1%) in the filtrate. In the ultrafiltration and the dialysis a distinction has to be made between the single passage and the recirculation.

With regard to the membrane of the catheter it is favourable if the membrane is a selectively permeable membrane which is permeable at least to the substance to be exchanged. In dependence on the application, i.e. in particular in dependence on the substance to be exchanged and, thus, also in dependence on the carrier liquid, the design, the material and the structure of the membrane can be adapted correspondingly. As materials there are suitable for instance hydrophilic or hydrophilized copolymers and hydrophilic polymer mixtures. In detail, as a membrane material there can be used mixtures with one or several components of a group consisting of polyethylene, thermoplastic polyurethane, polysulfones (PSU), polyethersulfones (PES), polyacrylethersulfones (PAES), polyvinyl pyrrolidone (PVP), polymethylmethacrylate (PMMA), polyamide (PA), polyacrylnitrile (PAN), and/or ethylene vinyl alcohol copolymer (EVOH), as well as cellulose, cellulose triacetate (CTA), or cellulose nitrate. It is preferred to use membranes substantially consisting only of PSU or PSE, substantially of a mixture of PES, PVP and PA (PEPA), or substantially of a mixture of PAES, PVP, and PA. The size of the pores of the membrane can lie between 0.01 µm and 0.1 µm. Additionally, the membrane can be coated, for instance with heparin.

A particularly large contact surface in a small space can be obtained if the membrane is a hollow fibre membrane. Here, the actual contact surface is formed by the walls of the hollow fibres or capillaries. A hollow fibre membrane can comprise up to 20,000 individual capillaries or hollow fibres. The diameter of the individual hollow fibres lies between 0.01 mm and 1 mm, in particular between 0.1 and 0.5 mm. The entire surface of the membrane, which forms the contact surface for the exchange of substances, lies between 0.01 and up to 10 $m^2$, preferably between 0.1 and 1 $m^2$. The material from which the hollow fibres are made can be composed of one or several of the above-mentioned components, wherein PMP (polymethylpentene) has to be mentioned as being preferred. In connection with the performance according to the invention and, if applicable, with the conveying of the blood through the catheter during operation, the filigree hollow fibres of the membrane can be accommodated in a protective catheter sheath. The flow resistance caused by the large contact surface can at least partially be compensated for by the conveying device.

Further preferred membrane materials can comprise nanocapsules or microcapsules or they can be manufactured by using such capsules. Nanocapsules can be produced by interfacial polymerization from polymers like polyacrylates, preferably poly(n-butyl cyanoacrylate) (PACA), as well as poly(lactid coglycolide) (PLGA), albumin. Such nanocapsules are characterized by a very small wall thickness of 3-20 nm. They can be filled with perfluorocarbons (PFC). Alternatively or additionally, also magnetic particles as well as fluorescence dyes (e.g. Nile red) can be added to the nanocapsules during the production thereof, so that they can be specified and identified in a better manner. (Delphine Moinard-Checot, Yves Chevalier, Stephanie Briancon et al. "Mechanism of nanocapsules formation by emulsion-diffusion process", Journal of Colloid and Interface Science 317 (2008) 458-468; Christian Erdmann, Christian Mayer, "Permeability profile of poly(alkyl cyanoacrylate) nanocapsules", Journal of Colloid and Interface Science 478 (2016) 394-401).

Microcapsules can for instance be produced from silicone, in particular from UV-curing silicone, for instance Semicosil 949UV, by means of a double-capillary method. Such microcapsules comprise an outer shell made of silicone and a filling. The filling can include sodium carbonate, potassium carbonate, magnesium carbonate, sodium chloride, physiological NaCl solution, as well as mixtures of the mentioned materials. The filling can further include carbonic anhydrase or chemical equivalents thereof, like cyclen Zn (II). The filling can also consist of PACA nanocapsules (as defined above) accommodated in a carrier medium. Furthermore, the filling of the microcapsules can substantially consist of pure perfluorocarbons or of emulsions of PFC. Fluorescence dyes can be added to the capsule material and/or to the filling. Furthermore, to the filling there can for instance also be added colour indicators (e.g. thymol blue)

which indicate a change in the pH value by a change in colour, in order to be able to monitor the saturation of the substances. (A. S. Utada, E. Lorenceau, D. R. Link, P. D. Kaplan, H. A. Stone, D. A. Weitz, "Monodisperse Double Emulsions Generated from a Microcapillary Device", SCIENCE VOL 308 22 Apr. 2005; John J. Vericella, Sarah E. Baker,*, Joshuah K. Stolaroff et al., "Encapsulated liquid sorbents for carbon dioxide capture", nature communications, 2015, DOI: 10.1038/ncomms7124).

Such nanocapsules and/or microcapsules can for instance be attached to the surface of membrane materials, like polymethylpentene (PMP), polypropylene (PP), or silicone, by means of polymers, cyanoacrylates, silicone (Loctite etc.). Thereby a chemical bond between the carrier material and the capsules is created which contributes to a surface enlargement and breaks the diffusion boundary layer by minimum turbulences. Correspondingly, the membrane of the present catheter can be provided with nanocapsules and/or microcapsules.

Alternatively or additionally, such nanocapsules and/or microcapsules can also be introduced into existing polymers like silicone in that they are for instance mixed or stirred thereinto. They spread out in the basic material and form for instance cavities filled with PFC which increase the permeability of the basic material. Alternatively, the nanocapsules and/or the microcapsules can be introduced between two thin polymer layers, preferably silicone (Silpuran). Thereby there are formed bubble foils. This increases the stability of the capsules. The materials thus produced are particularly suitable for the use as a membrane of the present catheter.

Furthermore, the microcapsules and/or nanocapsules can be bonded with each other, for instance by means of polymers, cyanoacrylates or silicone (Loctite etc.), and can thus be used for the production of foils or small hollow tubes, which foils and small hollow tubes can be used as a membrane of the present catheter.

The device according to the invention is particularly suitable for minimally invasive applications, for instance in the arm and leg veins. In this regard, the dimensions of the device according to the invention follow the dimensions which are used in the catheter technology (e.g. an outer diameter of 2.3 to 12.7 mm or 7 to 40 Fr). The design for the application in veins is preferred, wherein an outer diameter of the device of 10 mm or less, preferably of 8.7 mm or less, in particular of 8.0 mm or less, has proven to be especially well-suited in practice. Also the length of the device according to the invention preferably follows the standard vein catheter formats, i.e. approximately 100 to 400 mm, in particular 150 to 250 mm (in the blood vessel). The same applies to the materials which are used for the outer side; also here there shall be used the materials already known from the catheter technology.

In order to nevertheless keep the flow resistance and, thus, the output of the conveying device—which is required for the complete compensation—low, it is advantageous if the fibres of the hollow fibre membrane for the most part are arranged substantially in parallel to a longitudinal extension of the catheter. Here, the longitudinal extension of the catheter naturally corresponds to the main flow direction of the blood in the vessel surrounding the catheter during operation.

A simple possibility to provide the inflow and the outflow of the carrier medium at the same—preferably the distal—end of the catheter is that the membrane, in particular the hollow fibre membrane, is folded. With a folding by 180° at the opposing (proximal) end of the catheter, both ends of the hollow fibres are located at the same end of the catheter.

Even if principally also the use of a disposable catheter with a—apart from the membrane—closed reservoir for the carrier medium is conceivable and also enjoys the advantages according to the invention, it is favourable if the catheter has an inlet and an outlet for the carrier liquid which are connected with an extracorporeal exchange device for the formation of a circulation or circuit system with the exchange device, wherein the circulation system has a pump for the conveying of the carrier liquid. In this case it refers to a double-lumen catheter. Such exchange devices and circulation or circuit systems are principally known, wherein reference is made in particular to applications for the support of the pulmonary function (ECMO, ECCO2R) and dialysis applications.

In connection with the application as a lung support, it is favourable if the exchange device is a membrane oxygenator. The exchange device can, however, also be an absorber (for the removal of $\beta_2$ microglobulin, rheumatoid factors, lipids, immunoglobulins, or endotoxins), e.g. activated carbon absorbers or resin absorbers, it can be membrane devices for the diffusion, ultrafiltration, and/or convection of substance from the carrier medium, or it can be other filter devices.

Preferably, such a device can be made available together with a catheter and an extracorporeal exchange device in a kit, wherein the kit comprises additionally at least one tube connected with the catheter and the exchange device for the transport of a carrier liquid between the catheter and the exchange device. In this connection the tube preferably has at least two channels or lines, wherein an entry channel for the supply of the carrier liquid to the catheter and an exit channel for discharging the carrier liquid from the catheter are installed.

A particularly simple and continuous application is facilitated if, in the kit, the exchange device is a portable exchange device, preferably with a carrying means. As a carrying means there can be provided for instance fastening elements for a wrist strap or for the fastening at a belt or at another piece of clothing.

With regard to the method according to the invention is particularly favourable if the substance to be withdrawn for diagnostic purposes is a disease indicator, whereby also endogenous substances the presence of which (e.g. antibodies) or the quantity of which (e.g. inflammatory proteins, cytokines, complement factors, etc.) is correlated with a disease or its course, are comprised, in particular for instance at least a pathogen or at least an antibody, a substance which is toxic to the body (e.g. glucose or electrolytes outside the physiological range, like potassium, calcium, etc.), a substance which can otherwise not be excreted by the body (see storage diseases regarding glucose, copper, etc.), or in general an endogenous substance the quality or quantity of which correlates with the course of a disease, in particular at least a protein which is specific to a disease, or a substance generated by the courses of diseases (e.g. complement, cytokines, interleukins, or antibodies). When the substance is for instance glucose, the method can for instance be part of a diagnosis method for measuring the blood glucose.

In the following, preferred embodiments of the device according to the invention and of the method according to the invention as well as preferred combinations thereof will be stated:

1. A device comprising a catheter for intravascular use, wherein the catheter has a blood inlet and a blood outlet, and comprises a membrane, wherein a first side of the membrane is in contact with a carrier medium and wherein the membrane is arranged in the catheter in such a way that at least one part of the blood flowing into the catheter via the blood inlet during operation comes into contact with a second side of the membrane lying opposite the first side thereof, before the blood leaves the catheter via the blood outlet, wherein the membrane allows an exchange of at least one substance to be exchanged between the carrier medium and the blood, and wherein the catheter comprises a conveying device which is configured to at least partially compensate for a pressure difference between the blood inlet and the blood outlet, characterized in that the carrier medium is a carrier liquid in which the substance to be exchanged can be dissolved.

2. The device according to embodiment 1, characterized in that the conveying device comprises a drive unit for generating a torque and a pump rotor connected with the drive unit for the transmission of a torque.

3. The device according to embodiment 2, characterized in that the drive unit comprises an electric motor.

4. The device according to embodiment 2, characterized in that the drive unit comprises a turbine element around which the carrier medium flows during operation.

5. The device according to anyone of embodiments 2 through 4, characterized in that the pump rotor is connected to the drive unit via a magnetic coupling, wherein the magnetic coupling comprises two coupling parts for the transmission of the torque along an axis of rotation being rotatable relative to each other and each including a permanent magnet.

6. The device according to embodiment 5, characterized in that one of the coupling parts comprises an at least partially ferromagnetic guiding element which is non-rotatably connected to the permanent magnet of the coupling part, wherein one part of the guiding element is disposed radially outside of the permanent magnet of the other coupling part.

7. The device according to embodiment 6, characterized in that the guiding element comprises at least one diamagnetic separation parting the guiding element into at least two ferromagnetic sections.

8. The device according to anyone of embodiments 5 through 7, characterized in that the two coupling parts are hermetically separated.

9. The device according to anyone of embodiments 1 through 8, characterized in that the substance to be exchanged is $CO_2$ wherein the carrier liquid has a solubility of at least 140 ml $CO_2$, in particular of at least 180 ml $CO_2$, in 100 ml of the carrier liquid at 37° C.

10. The device according to anyone of embodiments 1 through 9, characterized in that the carrier liquid is a perfluorocarbon or an albumin solution and/or an electrolyte solution, in particular enriched with specific proteins or glucose derivatives, or that it is a commercially available dialysate which preferably was additionally processed via an ion exchanger, activated carbon or another adsorber.

11. The device according to anyone of embodiments 1 through 10, characterized in that the carrier liquid comprises an decoupler substance.

12. The device according to anyone of embodiments 1 through 11, characterized in that the membrane is a selectively permeable membrane which is permeable to at least the substance to be exchanged.

13. The device according to anyone of embodiments 1 through 12, characterized in that the membrane is a hollow fibre membrane.

14. The device according to embodiment 13, characterized in that the hollow fibres of the hollow fibre membrane for the most part are arranged substantially in parallel to a longitudinal extension of the catheter.

15. The device according to anyone of embodiments 1 through 14, characterized in that the membrane is folded.

16. The device according to anyone of embodiments 1 through 15, characterized in that nanocapsules or microcapsules are bonded with the surface of the membrane.

17. The device according to anyone of embodiments 1 through 16, characterized in that the membrane comprises nanocapsules or microcapsules, wherein the nanocapsules or the microcapsules are embedded in an otherwise homogeneous carrier material, or that the membrane consists of nanocapsules or microcapsules which are bonded with each other.

18. The device according to anyone of embodiments 1 through 17, characterized in that the catheter has an inlet and an outlet for the carrier liquid which are connected with an extracorporeal exchange device for the formation of a circulation system with the exchange device, wherein the circulation system has a pump for the conveyance of the carrier liquid.

19. The device according to embodiment 18, characterized in that the exchange device is a membrane oxygenator.

20. A kit comprising a device according to anyone of embodiments 18 or 19 and at least one tube connected with the catheter and the exchange device for the transport of a carrier liquid between the catheter and the exchange device.

21. The kit according to embodiment 20, characterized in that the exchange device is a portable exchange device, preferably with a carrying means.

22. A device comprising a catheter for intravascular use, wherein the catheter has a blood inlet and a blood outlet, and comprises a membrane, wherein a first side of the membrane delimits a lumen for the reception of a carrier medium, and wherein the membrane is arranged in the catheter in such a way that at least one part of the blood flowing into the catheter via the blood inlet during operation comes into contact with a second side of the membrane lying opposite the first side thereof, before the blood leaves the catheter via the blood outlet, wherein the membrane allows an exchange of at least one substance to be exchanged between a carrier medium received in the lumen during operation and the blood, characterized in that the lumen for the reception of a carrier liquid in which the substance to be exchanged can be dissolved is designed as a carrier medium, and that the membrane allows an exchange between the carrier liquid and the blood during operation.

23. The device according to embodiment 22, characterized in that the membrane is a membrane which is suitable for liquids.

24. The device according to embodiments 22 or 23, characterized in that the membrane is designed for the use with a perfluorocarbon or an albumin solution and/or an electrolyte solution, in particular enriched with specific proteins or glucose derivatives, or with a commercially available dialysate which preferably was additionally processed via an ion exchanger, activated carbon or another adsorber, as a carrier liquid.

25. The device according to anyone of embodiments 22 through 24, characterized in that the catheter comprises a conveying device which is configured to at least partially compensate for a pressure difference between the blood inlet and the blood outlet during operation.

26. A device comprising a catheter for intravascular use, wherein the catheter has a blood inlet and a blood outlet, and comprises a membrane, wherein a first side of the membrane is in contact with a carrier medium and wherein the membrane is arranged in the catheter in such a way that at least one part of the blood flowing into the catheter via the blood inlet during operation comes into contact with a second side of the membrane lying opposite the first side thereof, before the blood leaves the catheter via the blood outlet, wherein the membrane allows an exchange of at least one substance to be exchanged between the carrier medium and the blood, characterized in that the carrier medium is a carrier liquid in which the substance to be exchanged can be dissolved.

27. A method for removing at least one substance from venous blood for diagnostic purposes using a device or a kit according to anyone of embodiments 1 through 26, wherein the substance to be removed corresponds to the substance to be exchanged through the membrane of the catheter of the device.

28. The method according to embodiment 27, wherein the substance to be removed is a disease indicator, in particular at least a pathogen, at least an antibody, a substance which is toxic to the body, a substance which can otherwise not be excreted by the body, or an endogenous substance the quality or quantity of which correlates with the course of a disease, in particular at least a protein which is specific to a disease, or a substance generated by the courses of diseases.

29. A method for the treatment of a human or animal body by replacing or exchanging at least one substance from the blood or into the blood of the body using a device or a kit according to anyone of embodiments 1 through 26.

30. A use of the device according to anyone of embodiments 22 through 25 with a liquid carrier medium.

31. The use according to embodiment 30, characterized in that the liquid carrier medium is a perfluorocarbon or an albumin solution and/or an electrolyte solution, in particular enriched with specific proteins or glucose derivatives, or that it is a commercially available dialysate which preferably was additionally processed via an ion exchanger, activated carbon or another adsorber.

32. The use according to embodiments 30 or 31, characterized in that the liquid carrier medium comprises an decoupler substance.

Figure 7:
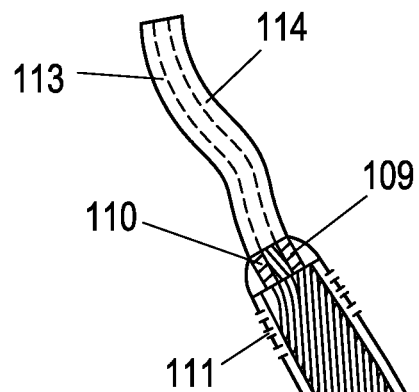
Figure 8:
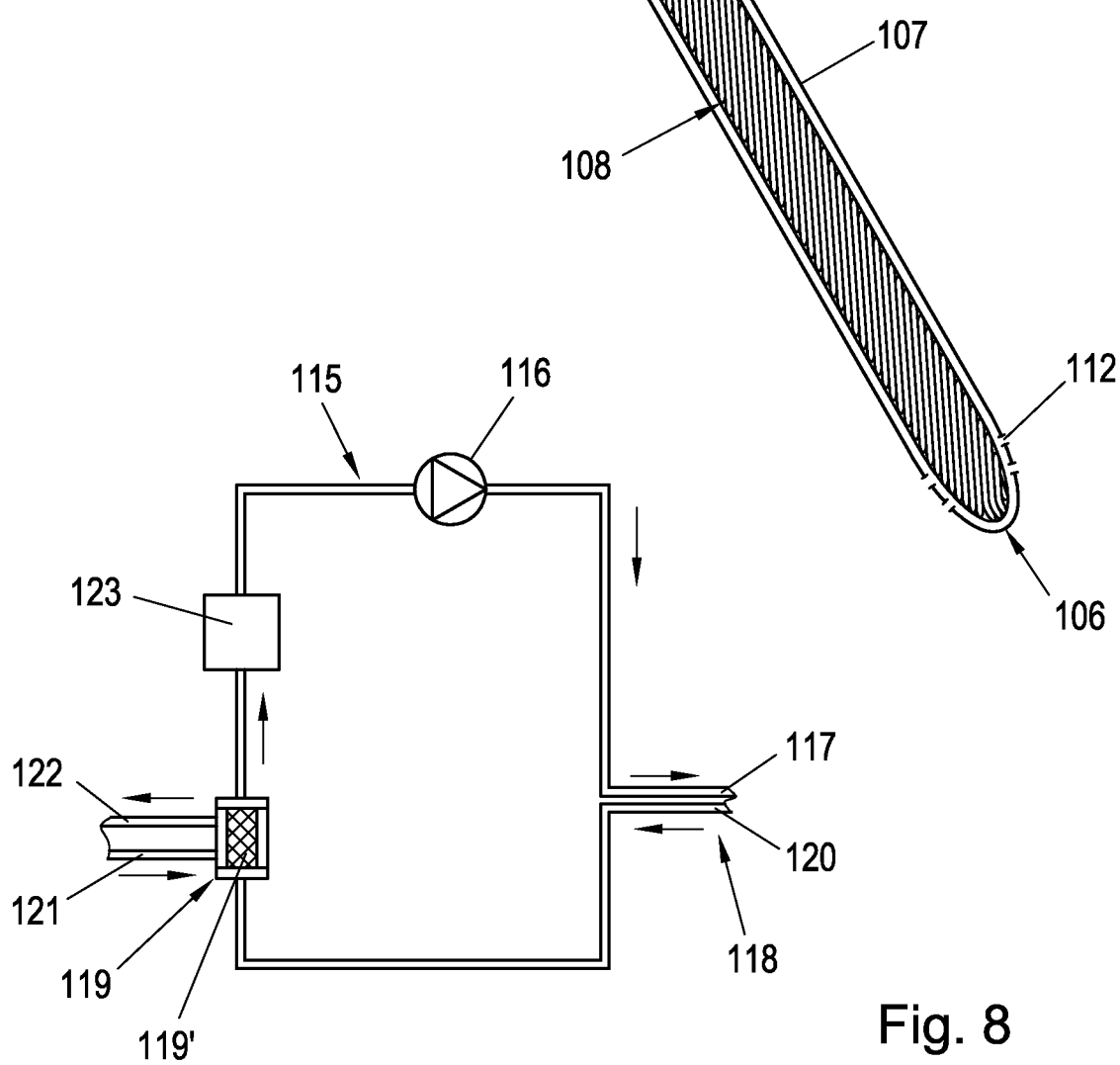

In the following, the invention will be explained still further by means of particularly preferred embodiments to which it shall, however, not be restricted, and with reference to the accompanying drawings. Individually, in the drawings:

FIG. 1 schematically shows a longitudinal section through a device with an intravascular catheter having a lateral blood inlet and a centrally arranged hollow fibre membrane;

FIG. 2 schematically shows a longitudinal section through a device with an intravascular catheter having a central blood passage, laterally arranged hollow fibre membranes, and a proximal reflux lumen;

FIG. 3 schematically shows a cross-section through the catheter along line III-III in FIG. 2;

FIG. 4 schematically shows a longitudinal section through a device with an intravascular catheter having a central blood passage and laterally arranged hollow fibre membranes without a proximal reflux lumen;

FIG. 5 schematically shows a longitudinal section through a device according to FIG. 4 with a motor-driven conveying device at the distal end of the blood passage;

FIG. 6 schematically shows a longitudinal section through a device with an intravascular catheter having laterally arranged hollow fibre membranes, lateral blood inlets and a turbine-driven conveying device at the distal end of the catheter;

FIG. 7 shows a further design variant of an intravascular catheter with a twisted hollow fibre membrane; and FIG. 8 schematically shows an extracorporeal circulation system for use with a catheter according to anyone of FIGS. 1 through 7.

In FIG. 1 there is schematically shown a device 1 with an intravascular catheter 2 in a longitudinal section. The catheter 2 is provided for being inserted through a vein and being positioned in the inferior or superior vena cava. The catheter 2 can in principle be of a usual design and has those properties which are required for its use or application. The catheter 2 comprises a catheter tube 3. The catheter tube 3 has a cross-section which is substantially circular in the relaxed state. The diameter of the catheter tube 3 is adapted to a vein, in particular it is smaller than the diameter of a vein in which the catheter shall be used. The catheter tube 3 consists of an elastic material which is commonly used for catheters, for instance of a biocompatible polyurethane. In the catheter tube 3 a membrane 4', in particular a hollow fibre membrane 4, extending lengthwise of the catheter tube 3 is arranged. For the sake of simplicity, the hollow fibre membrane 4 is only represented with one individual hollow fibre 5, and, in practice, it comprises a plurality of semipermeable hollow fibres consisting of one of the preferred membrane materials mentioned at the beginning. When, in the following, the function of the hollow fibre 5 is described, the respective explanations equally apply to a second and each further hollow fibre of the hollow fibre membrane 4. The hollow fibre membrane 4 is designed such that at the distal end 6 of the catheter 2 the carrier liquid can be introduced into the hollow fibre membrane 4 via an inlet 7 for a carrier liquid, said carrier liquid passing through the hollow fibre 5 of the hollow fibre membrane 4, and that the carrier liquid can be discharged via an outlet 8 for the carrier liquid. Therefore, the carrier liquid passes through the hollow fibre membrane 4 or its hollow fibre 5 between the inlet 7 and the outlet 8. Hence, the inner side of the hollow fibre 5 forms a first side of the hollow fibre membrane 4 which is in contact with the carrier liquid. The ends 9 of the hollow fibre 5 are fixed by an embedding mass 11 in a connecting area 10 and are connected with the embedding mass 11, for instance an epoxy resin. In the region of a proximal end 12 of the catheter, the hollow fibre 5 has a bend 13 so that the hollow fibre 5 has a continuous loop-like extension between the inlet 7 and the outlet 8.

The intravascular catheter 2 is further designed such that blood can flow around it and can pass through it. For this purpose, the catheter tube 3 has at least one lateral blood inlet 14 just outside the connecting area 10 at the distal end 6. At the proximal end 12 the catheter tube 3 is opened so that the opening forms a blood outlet 15. The blood flow in the catheter 2, into the catheter 2 and out of the catheter 2 is indicated by direction arrows 16. In this connection, the blood flows around the hollow fibre 5 of the hollow fibre membrane 4 starting from the lateral blood inlet 14 so that at least one part of the blood flowing into the catheter 2 via the blood inlet 14 during operation comes into contact with an outer side of the hollow fibre 5, which outer side forms a second side of the hollow fibre membrane 4 lying opposite to the first side thereof. Due to the material of the hollow fibre 5, said hollow fibre 5 and, thus, the hollow fibre membrane 4 as a whole allow an exchange of at least one substance to be exchanged between the carrier liquid inside the hollow fibre 5 and the blood surrounding it.

The inlet 7 and the outlet 8 are connected in a connection region 17 with a feeding tube 18. The feeding tube 18 has a coaxial inner tube 19. In the embodiment represented in FIG. 1, the channel formed inside the inner tube 10 serves as a supply channel 20, and the channel formed between the inner tube 19 and the outer jacket of the feeding tube 18 serves as a discharge channel 21 for the carrier liquid. The feeding tube is connected with the catheter 2 in the connection region 17 by means of an elastic connecting mass 22, for instance polyurethane.

In FIGS. 2 and 3 there is schematically shown a further embodiment of a device 22 with an intravascular catheter 23 having a central blood passage 24. The basic design of the catheter 23 with one catheter tube 25 corresponds to the catheter 2 and the catheter tube 3 described in connection with FIG. 1, unless it will be described differently in the following.

The central blood passage 24 extends as an open channel along a longitudinal axis in the centre of the catheter 23. Thus, the blood passage 24 connects a central blood inlet 26 at the distal end 27 of the catheter 23 and a central blood outlet 28 at the proximal end 29 of the catheter 23 in parallel to the catheter tube 25.

In the catheter 23 there is arranged a substantially cylindrical hollow fibre membrane 30, wherein the semipermeable hollow fibres 31, 32 are arranged around the central blood passage 24 and substantially in parallel to the longitudinal extension of the catheter 23. For the sake of simplicity, the hollow fibre membrane 30 is only represented with two individual hollow fibres 31, 32, and, in practice, it comprises a plurality of semipermeable hollow fibres consisting of one of the preferred membrane materials mentioned at the beginning. The first hollow fibre 31 is connected to a supply channel 33 of a feeding tube 34 at the distal end 27 of the catheter 23. The second hollow fibre 32 is connected to a discharge channel 35 of the feeding tube 34 at the distal end 27 of the catheter 23. When, in the following, the function of the first or second hollow fibre 31, 32 is described, the respective explanations equally apply to each of a first part of all further hollow fibres of the hollow fibre membrane 30 in accordance with the first hollow fibre 31 or of a second part of all further hollow fibres of the hollow fibre membrane 30 in accordance with the second hollow fibre 32.

In correspondence with the catheter 2 in FIG. 1, the first ends of all hollow fibres 31, 32 are fixed in a first ring-shaped connecting area 36 at the distal end 27 of the catheter 23 by an embedding mass 37 and they are connected with the embedding mass 37, for instance an epoxy resin. At the proximal end 29 of the catheter 23 there are fixed the second ends of all hollow fibres 31, 32 in a second ring-shaped connecting area 38 also by means of an embedding mass 39 and they are connected with the embedding mass 39, for instance an epoxy resin. The hollow fibres 31, 32 are connected to a reflux lumen 40 at their second ends, said reflux lumen 40 being formed at the distal end 29 of the catheter 23 as a ring-shaped channel within the catheter tube 25. Thus, the hollow fibre membrane 30 is designed in such a way that a carrier liquid introduced at the distal end 27 of the catheter 23 via an inlet 41 into the hollow fibre membrane 30 passes through the first hollow fibre 31 of the hollow fibre membrane 30, changes at the proximal end 29 of the catheter over to the reflux lumen 40, is guided to the second hollow fibre 32, passes through the second hollow fibre 32 and is discharged via an outlet 42.

Thus, the inner side of the hollow fibres 31, 32 forms a first side of the hollow fibre membrane 30 which is in contact with the carrier liquid. The blood flow in the catheter 23, into the catheter 23 and out of the catheter 23 is indicated by direction arrows 43. In this connection, the blood flows around the hollow fibres 31, 32 of the hollow fibre membrane 30 starting from the central blood passage 24 so that at least one part of the blood flowing into the catheter 23 via the blood inlet 26 during operation comes into contact with an outer side of the hollow fibres 31, 32, which outer side forms a second side of the hollow fibre membrane 30 lying opposite the first side thereof. Due to the materials of the hollow fibres 31, 32, said hollow fibres and, thus, the hollow fibre membrane 30 as a whole allow the exchange of at least one substance to be exchanged between the carrier liquid inside the hollow fibres 31, 32 and the surrounding blood.

In FIG. 4 there is shown another alternative design variant of the device according to the invention with a catheter 44. The basic design of the catheter 44 with a catheter tube 45 corresponds again to the catheter 2 or 23 described in connection with FIGS. 1 to 3, unless it will be described differently in the following.

In contrast to the above described catheters 2, 23, according to FIG. 4 the hollow fibre membrane 46 of the catheter 44, which forms the membrane 4' of the catheter, is arranged cylindrically around a central blood passage 24 like in FIG. 2, but the individual hollow fibres 47, 48 are formed loop-like—as in FIG. 1—with a bend 13 in the region of a proximal end 49 of the catheter 45. Hence, the arrangement of the hollow fibre membrane 46 corresponds to a cylinder turned to the outside at half the height. The ends 50, 51 of the hollow fibres 47, 48 are fixed in a ring-shaped connecting area 52 by an embedding mass 53, and they are connected with the embedding mass 53, for instance an epoxy resin. The ends 50 of the hollow fibres 47, 48 which lie radially inside with respect to a central longitudinal axis of the catheter 45 lead into a ring-shaped inlet 54 of the hollow fibre membrane 46 for a carrier liquid. The ends 51 of the hollow fibres 47, 48 which lie radially outside with respect to a central longitudinal axis of the catheter 45 correspondingly lead into a ring-shaped outlet 55 of the hollow fibre membrane 46 for a carrier liquid, wherein said ring-shaped outlet 55 is arranged concentrically to the inlet 54 and radially outside thereof. The inlet 54 of the hollow fibre membrane 46 is connected with a supply channel 56 of a feeding tube 57. The outlet 55 of the hollow fibre membrane 46 is connected with a discharge channel 58 of the feeding tube 57. Otherwise, the feeding tube 57 is designed in a manner identical to that of the feeding tube 18 according to FIG. 1.

In the represented example, the channels 56, 58 of the feeding tube 57 end at two radially opposing locations in the ring-shaped inlet 54 and the ring-shaped outlet 55 so that the feeding tube 57 is bifurcated into two tube branches 60 at the connection region 59. The carrier liquid introduced via the inlet 54 into the hollow fibre membrane 46 passes through the hollow fibres 47, 48 of the hollow fibre membrane 46 in parallel to the longitudinal extension of the catheter 45 up to the bend 13 of the hollow fibres 47, 48 and back to the distal end 61 of the catheter and is discharged via the outlet 55.

Radially inside the inlet 54 of the hollow fibre membrane 46, the catheter 45 has a central blood inlet 62 into the blood passage 24 at the distal end 61 thereof. At the proximal end 49, the catheter tube 44 is opened so that the opening forms a blood outlet 15 as in FIG. 1. The blood flow in the catheter 45, into the catheter 45 and out of the catheter 45 is indicated by direction arrows 63. In this connection, the blood flows around the hollow fibres 47, 48 of the hollow fibre membrane 46 starting from the blood inlet 62 so that at least one part of the blood flowing into the catheter 45 via the blood inlet 62 during operation comes into contact with an outer side of the hollow fibres 47, 48. In order to avoid repetitions, with regard to the exchange of substances with the blood reference is made to the respective explanations with respect to FIGS. 1 and 2 and the membranes shown therein.

Since the devices in FIGS. 1 to 4 have been shown and described without conveying devices for the sake of simplicity, now FIGS. 5 and 6 each show a conveying device 64, 65 which can be used in particular in the catheters 23 or 44 as shown in FIGS. 2 and 4, preferably in the blood inlet 26 or 62, respectively. Accordingly, the catheters 44 are represented in FIG. 5 and FIG. 6 only sketchily, and with regard to the design and the functioning of the catheter 44 as well as of the membranes arranged therein reference is made to the earlier explanations in connection with FIGS. 1 to 4.

The conveying device represented in FIG. 5 comprises a pump rotor 66 and a drive unit 67 in the form of an electric motor 68. During operation, the electric motor 68 transmits a torque via a shaft 69 to the pump rotor 66. The shaft 69 is supported by means of an end 70 lying opposite the electric motor 68 in a stator 71. The stator 71 is fastened in the catheter 44 in a connecting area 52 via wings 72. Here, the wings 72 are arranged substantially in parallel or slightly angled to a flow direction (indicated by the direction arrows 73) of the blood entering through the lateral blood inlets (not shown) into the catheter 44. The pump rotor 66 itself also has blades 74 which are arranged propeller-like for the axial transport of the blood located between the blades 74 during a rotation of the pump rotor 66.

During operation, the pump rotor 66 is driven by the electric motor 68—which forms a drive unit 85'—in such a way that an acceleration of the blood flow in the area of the blood inlets and, thus, an excess pressure at the distal end 61 of the catheter 44 are generated. In this connection, the rotational speed of the electric motor 68 is controlled via a control (not shown) such that the obtained excess pressure just compensates for a pressure difference between the blood inlets and the blood outlet 15 (see FIG. 5). Thereby the flow resistance caused by the hollow fibres 47, 48 inside the catheter 44 is effectively compensated for. Thus, the amount of blood moved through the lumen of the catheter 44 corresponds to the same amount which would be moved through the hollow catheter tube 45 if the catheter had no membrane.

For the fixation with respect to the stator 71, the electric motor 68 is embedded in an embedding mass 76 which connects the electric motor with the catheter tube 44.

FIG. 6 shows a further, preferred embodiment for a conveying device 65. The conveying device 65 forms the distal end 77 of the catheter 44. The conveying device 65 comprises a pump rotor 78 which is rotatably arranged between a magnetic coupling 79 and a pump stator 80 and is rotatably supported with a shaft 81 in the pump stator 80. The pump stator 80 is fastened via lateral wings 82 in a first connecting ring 83. The first connecting ring 83 comprises an embedding mass 84 in which the hollow fibres 47, 48 of the hollow fibre membrane 46 are embedded and with which they are connected, wherein the hollow fibres 47, 48 extend through the first connecting ring 83 axially, i.e. in parallel to a longitudinal axis of the catheter 44. The first connecting ring 83 is connected at a radial outer side to the catheter tube 45 of the catheter 44.

The conveying device 65 further comprises as a drive unit 85' a turbine element 85 which is supported in a turbine stator 86 such that it is rotatable around a shaft 87. The shaft 87 forms a non-rotatable connection of the turbine element 85 with the magnetic coupling 79, in particular with a drive-side coupling part 88. The turbine stator 86 is arranged between the drive-side coupling part 88 and the turbine element 85 which acts as a turbine rotor, wherein the shaft 87 extends through the turbine stator 86. The turbine stator 86 has lateral wings 89 by means of which it is fastened in a section 91 of the inner tube 92 of a feeding tube 93, said section 91 being widened in the connecting area 90. Correspondingly, the turbine element 85 is also arranged in the widened section 91, and, thus, it is subjected to the flow of a carrier liquid 95 supplied through a supply channel 94 of the feeding tube 93. As is indicated by the direction arrows 95, the flow of the carrier liquid 95 leads out of the supply channel 94 into the widened section 91 via propeller-like blades 97 arranged at the turbine element 85 for the reception of a torque and past the wings 89 of the turbine stator 86 to the inlet 54 of the hollow fibre membrane 46.

The ring-shaped inlet 54 and outlet 55 of the hollow fibre membrane 46 is formed at a second connecting ring 98 which—comparable to the connecting area 52 in FIG. 4—comprises an embedding mass 99 in which the ends 50, 51 of the hollow fibres 47, 48 are embedded so that they lead into the inlet 54 or into the outlet 55. Between the second connecting ring 98 and the first connecting ring 83 which is arranged proximal of the second connecting ring 96, the catheter 44 has lateral blood inlets 100.

Apart from the drive-side coupling part 88, the magnetic coupling 79 also comprises a corresponding output-side coupling part 101 which is non-rotatably connected to the pump rotor 78. Due to the rotatable support via the separated shafts 81, 87 in the stators 80, 86, the drive-side coupling part 88 is rotatably supported relative to the output-side coupling part 101. The output-side coupling part 101 comprises an output-side two-pole permanent magnet 102 which is non-rotatably connected to the shaft 81 of the pump rotor 78. The drive-side coupling part 88 comprises a drive-side two-pole permanent magnet 103 which is non-rotatably connected to the shaft 87 of the turbine element 85. The output-side permanent magnet 102 is circumferentially surrounded by a substantially cup-shaped guiding element 104 having a hollow cylindrical jacket. In this connection, there is provided a clearance or gap between the output-side permanent magnet 102 and the guiding element 104 so that the output-side coupling part 101 is coupled to the drive-side coupling part 88 in a contact-free fashion. The guiding element 104 is mainly made of a ferromagnetic material. The jacket of the guiding element 104 is interrupted by a diamagnetic separation (not shown) only in a narrow angular region. Substantially, the separation parts the guiding element 104 into two ferromagnetic halves or half-shells. An intersecting plane running through the separation is thus perpendicular to a direction of magnetisation of the drive-side two-pole permanent magnet 103 that is connected to the guiding element 104. Consequently, the ferromagnetic sections of the guiding element 104 defined by the separation are magnetised in accordance with the drive-side permanent magnet 103.

Due to the contact-free coupling there is provided a hermetic separation (not shown) between the drive-side coupling part 88 and the output-side coupling part 101. The hermetic separation is formed by a foil sealingly connected with the radial inner side of the second connecting ring 98.

During operation, by the flow of the supplied carrier liquid a torque is applied via the blades 97 to the turbine element 85. The turbine element 85 transmits the torque via the shaft 87 to the drive-side coupling part 88 of the magnetic coupling 79. By the magnetic forces between the coupling parts 88, 101, the torque is transmitted from the drive-side coupling part 88 to the output-side coupling part 101, wherein the power of the magnetic forces defines a certain maximum transmittable torque beyond which a "slipping" of the coupling parts 88, 101 relative to each other occurs. The output-side coupling part 101 transmits a torque exerted by the drive-side coupling part 88 via the shaft 81 to the pump rotor 78. By means of lateral propeller-like blades 105, the pump rotor 78 transports the blood located between the blades 105 from the blood inlets 100 in the direction of the blood passage 24 inside the catheter 44. In this way, the conveying device 65 generates a pressure difference between the blood inlets 100 and the proximal end of the blood outlet 24 which preferably and substantially completely compensates for a pressure difference between the proximal and the distal end (not shown) of the catheter 44 which is due to the flow resistance of the hollow fibre membrane 46. Here, the turbine element 85 and the pump rotor 78 are preferably tuned with each other such that an optimum ratio between the flow velocity of the carrier liquid in the hollow fibres 47, 48 and the flow velocity of the blood in the blood passage 24 is obtained.

In the above embodiments, the two conveying devices 64, 65 are arranged in a region of the distal end 27, 77 of the catheter 44, respectively. As a matter of course, also arrangements at any location within the catheter 44 are conceivable, whereby, as expected, similar advantages can be achieved. Furthermore, of course also other arrangements than the shown arrangements of the respective rotors (pump rotor or turbine element) with regard to the respective stators or with several stators or altogether with only one stator are possible without leaving the functioning according to the invention and, thus, the scope of the invention.

Moreover, instead of a hollow fibre membrane also another type of membrane can be used in the catheter, wherein the person skilled in the art will adapt the conveying device 64, 65 to the pressure difference to be expected due to the different flow resistances of other types of membranes.

FIG. 7 shows another design variant of an intravascular catheter 106 which is provided for being inserted through a vein and for being positioned in the inferior or the superior vena cava. The catheter 106 can in principle be of a usual design and has those properties which are required for its use or application. Therefore, the catheter 106 comprises a catheter tube 107 formed in particular with a circular cross-section, the diameter of which is adapted to the diameter of the vein, in particular it is slightly smaller than the diameter of the vein. The catheter tube 107 consists of an elastic material which is commonly used for catheters, for instance of a biocompatible polyurethane. In the catheter tube 107 there is present a hollow fibre membrane module 108 extending lengthwise of the tube 107, with a hollow fibre membrane having a plurality of hollow fibres being permeable to gas but impermeable to liquids and consisting of one of the materials mentioned at the beginning, for instance polyethylene or thermoplastic polyurethane. The hollow fibre membrane module 108 is designed such that at the distal end of the catheter 106 a medium which flows through the hollow fibres can be fed via a first catheter connection 109 into the hollow fibre membrane 108, and that the medium can be discharged via a second catheter connection 110. Therefore, the medium which will be explained in detail below passes through the hollow fibre membrane module 108 between the first catheter connection 109 and the second catheter connection 110. FIG. 7 shows a possible design variant of the hollow fibre membrane module 108 as a bundle of hollow fibres which extends between the first catheter connection 109 and the second catheter connection 110 in a kind of a loop form along the inside of the catheter. Thus, the one ends of the hollow fibres are connected with the first catheter connection 109 and the second ends are connected with the second catheter connection 100. At the connecting areas, the hollow fibres can be cast or connected with each other by an epoxy resin or the like. The loop-like extending bundle of hollow fibres can additionally be twisted. Furthermore, the intravascular catheter 106 is designed such that blood can flow around it and can flow through it. For this purpose, the tube 107 can for instance be provided with a number of inflow openings 11 just outside the two catheter connections 109, 110 and can be provided with a number of outflow openings 112 in the region of its proximal end.

The hollow fibre membrane module 108 can be designed such that in one part of the hollow fibres the medium flows in a parallel flow with the blood and that in another part of the hollow fibres the medium flows in a counterflow to the blood. In the shown embodiment, the two catheter connections 109, 110 are shown such that they are coaxially positioned, but they can also be arranged next to each other in dependence on the design of the hollow fibre membrane module 108 (see FIG. 1 or FIG. 2).

Furthermore, the catheter connections 109, 110 are connected with flexible tubes extending in particular coaxially over one section, to which tubes a feeding tube 113 connected to the first connection 109 and a discharge tube 114 connected to the second connection 5 belong.

The catheters 2, 23, 44, 106 described and shown so far in FIGS. 1 through 7 can be a component of a larger device which, together with one of the catheters 2, 23, 44, 106, forms a circulation or circuit system 115 to which further, extracorporeal components belong. FIG. 8 schematically shows an embodiment of such extracorporeally provided components, namely a pump 116 which conveys a carrier liquid into the supply channel 117 of a feeding tube 118 and thus to the catheter (not shown in FIG. 8) and through it. The pump 116 is connected with the feeding tube 118. A further component is an oxygenator 119 in which the carrier liquid coming from the discharge channel 120 is introduced. The oxygenator 119 can be a conventional, standard membrane oxygenator 119' having a gas supply 121 and a gas discharge 122. In the extracorporeal part of the circuit there are further located for instance a heat exchanger 123 which heats the carrier liquid up to body temperature, as well as further components which are not shown, for instance pressure measuring devices, devices for the flow measurement, bubble detectors, etc.

During operation, in a vein the major part of the blood transported in the vein and enriched with $CO_2$ comes into contact with the hollow fibre membrane module 108 between the distal and the proximal end of the catheter 106. In this connection, the respective application-specific carrier liquid is pumped through the hollow fibre membrane module 108, wherein the carrier liquid of the hollow fibre membrane module 108 in part passes in the flowing direction of the blood and in part passes against the flowing direction of the blood. At the surfaces of the hollow fibres, for instance carbon dioxide ($CO_2$) transitions from the blood into the carrier liquid. The carrier liquid enriched with $CO_2$ leaves the hollow fibre membrane module 108 as well as the catheter 106 via the discharge channel 120 and is guided into the external oxygenator 119 where the carbon dioxide is passed over and oxygen is optionally added to the carrier liquid. In a simple embodiment, the external oxygenator 119 is supplied with ambient air. Through the gas exchange processes in the oxygenator 119, the liquid also absorbs oxygen from the ambient air so that oxygen is passed over to the passing blood in the hollow fibre membrane module 108. In an alternative embodiment of the invention, the liquid can be enriched with oxygen within the frame of its oxygen capacity by a supply of oxygen in the oxygenator 119. The carrier liquid heated up to body temperature is added again to the hollow fibre membrane module 108 in the circuit. The efficiency of the gas transfer in the hollow fibre membrane module 108 is particularly high due to the fact that the carrier liquid is pumped in the flowing direction of the blood as well as also against the flowing direction of the blood through the hollow fibre membrane module 108.

Analogously to the application for the exchange of $CO_2$, the device can also be used for the removal of other substances, e.g. endotoxins, from the blood. In this connection, as a carrier liquid a correspondingly suitable liquid (e.g. commercially available) dialysate or its preparation by activated carbon/ion exchanger/adsorber, or an isotonic liquid enriched with endotoxin-neutralizing protein (ENP), or albumin can be provided. Instead of a closed circulation or circuit system, the dialysate can be drawn from a reservoir, it can be pumped through the catheter and then it can be accumulated in a separate reservoir for the disposal thereof.

As a further alternative, in the closed circulation system 115 there can be provided instead of the oxygenator 119 or in addition to the oxygenator 119 a filtering unit, e.g. with an adsorption filter, so that a substance to be exchanged is separated in the filtering unit from the carrier medium.

The device according to the invention can be designed as a portable, small unit which can be carried along by the patient, in particular in a design in which ambient air is supplied to the external membrane oxygenator 119. The device according to the invention can furthermore be used in each conventional extracorporeal method as an additional device, above all also in conventional dialysis circuits.

The invention claimed is:

1. A device comprising a catheter for intravascular use, wherein the catheter has a blood inlet and a blood outlet, and comprises a membrane, wherein a first side of the membrane delimits a lumen for the reception of a carrier medium, and wherein the membrane is arranged in the catheter in such a way that at least one part of the blood flowing into the catheter via the blood inlet during operation comes into contact with a second side of the membrane lying opposite the first side thereof, before the blood leaves the catheter via the blood outlet, wherein the membrane allows an exchange of at least one substance to be exchanged between a carrier medium received in the lumen during operation and the blood, and wherein the catheter comprises a conveying device comprising a drive unit for generating a torque and a pump rotor connected with the drive unit for the transmission of a torque, wherein the conveying device is configured to at least partially compensate for a pressure difference between the blood inlet and the blood outlet during operation, wherein the membrane is a membrane which is suitable for liquids, wherein the carrier medium is a carrier liquid in which the substance to be exchanged can be dissolved, and that the pump rotor is connected to the drive unit via a magnetic coupling, wherein the magnetic coupling comprises two coupling parts for the transmission of the torque along an axis of rotation, said coupling parts being rotatable relative to each other and each including a permanent magnet, wherein one of the coupling parts comprises an at least partially ferromagnetic guiding element which is non-rotatably connected to the permanent magnet of the coupling part, wherein one part of the guiding element is disposed radially outside of the permanent magnet of the other coupling part, wherein the guiding element comprises at least one diamagnetic separation parting the guiding element into at least two ferromagnetic sections.

2. The device according to claim 1, wherein the drive unit comprises an electric motor.

3. The device according to claim 1, wherein the drive unit comprises a turbine element around which the carrier medium flows during operation.

4. The device according to claim 1, wherein it is designed for the use with perfluorocarbon or an albumin solution and/or an electrolyte solution, in particular enriched with specific proteins or glucose derivatives, or with a commercially available dialysate which preferably was additionally processed via an ion exchanger, activated carbon or another adsorber, as a carrier liquid.

5. The device according to claim 1, wherein the catheter has an inlet and an outlet for the carrier liquid which are connected with an extracorporeal exchange device for the formation of a circulation system with the exchange device, wherein the circulation system has a pump for conveying the carrier liquid.

6. A kit comprising the device according to claim 5 and at least one tube connected with the catheter and the exchange device for the transport of a carrier liquid between the catheter and the exchange device.

7. The kit according to claim 6, wherein the exchange device is a portable exchange device, preferably with a carrying means.

8. A method comprising removing at least one substance from venous blood for diagnostic purposes using the device according to claim 1, wherein the substance to be removed corresponds to the substance to be exchanged through the membrane of the catheter of the device.

9. The method according to claim 8, wherein the substance to be removed is a disease indicator, in particular at least a pathogen, at least an antibody, a substance which is toxic to the body, a substance which can otherwise not be excreted by the body, or an endogenous substance the quality or quantity of which correlates with a course of a disease, in particular at least a protein which is specific to a disease, or a substance generated by the courses of diseases.

10. A method for the treatment of a human or animal body comprising replacing or exchanging at least one substance from the blood or into the blood of the body using the device according to claim 1.

11. A method comprising using the device according claim 1 with a liquid carrier medium.

12. The method according to claim 11, comprising providing the liquid carrier medium as a perfluorocarbon or an albumin solution and/or an electrolyte solution, in particular enriched with specific proteins or glucose derivatives, or as a commercially available dialysate which preferably was additionally processed via an ion exchanger, activated carbon or another adsorber.

13. The method according to claim 11, comprising providing the liquid carrier medium as a decoupler substance.

* * * * *